United States Patent
Georgi et al.

(10) Patent No.: US 7,356,413 B2
(45) Date of Patent: Apr. 8, 2008

(54) PORE-SCALE GEOMETRIC MODELS FOR INTERPRETATION OF DOWNHOLE FORMATION EVALUATION DATA

(75) Inventors: Daniel T. Georgi, Houston, TX (US); Songhua Chen, Katy, TX (US); David Jacobi, The Woodlands, TX (US)

(73) Assignee: Baker Hughes Incorporated, Houston, TX (US)

(*) Notice: Subject to any disclaimer, the term of this patent is extended or adjusted under 35 U.S.C. 154(b) by 83 days.

(21) Appl. No.: 11/146,886

(22) Filed: Jun. 3, 2005

(65) Prior Publication Data

US 2006/0287201 A1 Dec. 21, 2006

(51) Int. Cl.
*G01V 11/00* (2006.01)

(52) U.S. Cl. ........................................ 702/11

(58) Field of Classification Search ............... 702/7, 702/9, 11, 12, 13; 703/10; 324/303
See application file for complete search history.

(56) References Cited

U.S. PATENT DOCUMENTS

| | | | |
|---|---|---|---|
| 3,321,625 A | 5/1967 | Wahl | 250/71.5 |
| 4,271,356 A | 6/1981 | Groeschel et al. | 250/262 |
| 4,953,399 A | 9/1990 | Fertl et al. | 72/152 |
| 5,303,775 A | 4/1994 | Michaels et al. | 166/264 |
| 5,452,761 A | 9/1995 | Beard et al. | 166/250 |
| 6,008,645 A | 12/1999 | Bowers et al. | 324/303 |
| 6,088,656 A | 7/2000 | Ramakrishnan et al. | 702/13 |
| 6,157,893 A | 12/2000 | Berger et al. | 702/9 |
| 6,557,632 B2 | 5/2003 | Cernosek | 166/264 |
| 2002/0173915 A1 | 11/2002 | Egermann et al. | 702/12 |
| 2003/0057947 A1 | 3/2003 | Ni et al. | 324/309 |
| 2003/0094946 A1 | 5/2003 | Galford et al. | 324/303 |
| 2003/0225521 A1 | 12/2003 | Panga et al. | 702/6 |
| 2003/0226663 A1 | 12/2003 | Krueger et al. | 166/252.5 |
| 2005/0178189 A1 | 8/2005 | Lenormand et al. | 73/38 |
| 2005/0206378 A1 | 9/2005 | Hamdan et al. | 324/303 |

OTHER PUBLICATIONS

Per H. Valvatne et al.; *Predictive Pore-Scale Network Modeling*, SPE 84550, SPE Annual Technical Conference and Exhibition, Oct. 5-8, 2003, pp. 1-12, 20 Figs.

Bryant et al.; *Prediction of elastic-wave velocities in sandstones using structural models*, Geophysics, vol. 60, No. 2 (Mar.-Apr. 1995),pp. 437-446, 11 Figs., 1 Table.

Fritz Gassmann; *Elastic Waves Through a Packing of Spheres*, Geophysics, vol. 16, Issue 4, Oct. 1951, pp. 673-685, 6 Figs.

Toumelin et al.; *A Numerical Assessment of Modern Borehole NMR Interpretation Techniques*, SPE 90539, SPE Annual Technical Conference and Exhibition, Sep. 26-29, 2004, pp. 1-19, 19 Figs.

M. Gladkikh et al.; *Mechanistic Prediction of Capillary Imbibition Curves*, SPE90333, SPE Annual Technical Conference and Exhibition, Sep. 26-29, 2004, pp. 1-7, 13 Figs.

(Continued)

*Primary Examiner*—Donald E McElheny, Jr.
(74) *Attorney, Agent, or Firm*—Hugh R. Kress; Arnold & Knobloch, L.L.P.

(57) ABSTRACT

Parameters of a pore-scale geometric model of a clastic earth formation are adjusted so that the output of the model matches measurements made on a core sample. Additional properties of the earth formation are predicted using the pore-scale model. The additional properties may be based on additional measurements of properties of a fluid in the formation.

27 Claims, 11 Drawing Sheets

OTHER PUBLICATIONS

Lecture notes; CENG 671, Rice University, Spring 2004, pp. 3-1-3-16.

B.F. Swanson; *A Simple Correlation Between Permeabilities and Mercury Capillary Pressures*, Journal of Petroleum Technology, Dec. 1981, pp. 2498-2504.

Steven L. Bryant et al.; *Network Model Evaluation of Permeability and Spatial Correlation in a Real Random Sphere Packing*, Transport in Porous Media 11: 1993, pp. 53-70.

Steven Bryant et al., *Quantification of Spatial Correlation in Porous Media and Its Effect on Mercury Porosimetry*, Journal of Colloid and Interface Science 177, (1996), pp. 88-100, 10 Figs.

Steven Bryant et al.; *Prediction of relative permeability in simple porous media*, Physical Review A, vol. 46, No. 4, Aug. 15, 1992, pp. 2004-2011, 6 Figs.

Martin J. Blunt et al.; *Detailed physics, predictive capabilities and macroscopic consequences for pore-network models of multiphase flow*, Elsevier, Advances in Water Resources 25 (2002), pp. 1069-1089.

PORE-SCALE GEOMETRIC MODELS FOR INTERPRETATION OF DOWNHOLE FORMATION EVALUATION DATA

CROSS-REFERENCES TO RELATED APPLICATIONS

This application is related to an application Ser. No. 11/147,063 being filed concurrently with the same inventors and the same title.

BACKGROUND OF THE INVENTION

1. Field of the Invention

The invention is related generally to methods of interpretation of properties of subterranean earth formations using measurements made by a formation evaluation sensor or sensors. Specifically, the invention is directed towards the use of modeling methods that enable the prediction of properties that are not measured by the formation evaluation sensor or sensors.

2. Background of the Art

Oil or gas wells are often surveyed to determine one or more geological, petrophysical, geophysical, and well production properties ("parameters of interest") using electronic measuring instruments conveyed into the borehole by an umbilical such as a cable, a wireline, slickline, drill pipe or coiled tubing. Tools adapted to perform such surveys are commonly referred to as formation evaluation (FE) tools. These tools use electrical, acoustical, nuclear and/or magnetic energy to stimulate the formations and fluids within the borehole and measure the response of the formations and fluids. The measurements made by downhole instruments are transmitted back to the surface.

In order to reduce the amount of rig time needed for wireline logging, it is common practice to run multiple sensors in a single run. FOCUS™, from Baker Atlas Inc., is a high efficiency premium open hole logging system. All of the downhole instruments have been redesigned, incorporating advanced downhole sensor technology, into shorter, lighter, more reliable logging instruments, capable of providing formation evaluation measurements with the same precision and accuracy as the industry's highest quality sensors, at much higher logging speeds. Logging speeds are up to twice the speed of conventional triple-combo and quad combo logging tool strings. Speeds of up to 3600 ft/hr (1080 m/min) are possible. The logging system may include four standard major open-hole measurements (resistivity, density, neutron, acoustic) plus auxiliary services.

Some petrophysical properties are easily obtained from downhole FE measurements. These include porosity, bulk density, NMR relaxation $T_1$ and $T_2$ spectra, and compressional and shear wave velocities. Other petrophysical properties that are of importance in reservoir evaluation and development are difficult if not impossible to measure. Properties that are difficult or impossible to measure include, for example permeability, relative permeability, resistivity formation factor, capillary pressure, and NMR surface relaxivity. These are typically derived from correlations or petrophysical relationships.

One of the problems with relating the different petrophysical properties of an earth formation to each other is that they are all macroscopically measured quantities that depend ultimately on the microscopic arrangement of the constituents of the earth formation. An early attempt at predicting macroscopic properties based on microscopic models is due to Gassmann (1951) in which the earth formation is modeled as a hexagonal close packing of equal-sized elastic spheres. Based on this simplistic model, it is possible to predict the stress dependence of the packing in terms of the moduli of the constituent spheres.

The earth, of course, is not made out of a hexagonal close packing of equal-size elastic spheres. Finney (1968) measured the spatial coordinates of some 8000 spheres in a random packing of spheres, thereby completely determining the geometry of the microstructure of the packing. This packing may be regarded as a physical model of a clean sediment of well-sorted sand grains. The term "sorting" refers to the distribution of grain sizes: a poorly sorted sandstone has a large range of grain sizes while a well sorted sandstone has grains of substantially the same size. Such sediments can be deposited in a wide spectrum of depositional environments, from nonmarine to basinal deep water. The model developed by Finney is primarily applicable to earth formations comprised of compacted clastic sediments. The term "clastic" refers to rocks made up of fragments of preexisting rocks. Based on the model of Finney, there have been numerous papers that discuss the prediction of formation properties. For example, Bryant and Raikes (1995) used the central core of 3367 spheres in Finney's pack, which has a porosity of 36.2% to try to predict elastic wave velocities in sandstones. In Toumellin et al. (2004), the NMR response of porous rocks was simulated using a continuous, three-dimensional (3D) random-walk algorithm. Diffusion pathways of individual fluid molecules are determined within the 3-D porous model. The method of Toumellin allows the rigorous treatment of $T_1$ and $T_2$ relaxation times with a minimum of assumptions and for arbitrary pulse sequences. Toumellin also discusses the numerical accuracy of the simulation. The results reproduce NMR decay and build-up while accounting for restricted diffusion in porous media, fluid wettabilities, and fluid spatial distributions.

By far the greatest amount of work using pore scale models has been in the area of determination of formation permeability. Valvatne et al. (2003) use pore-scale modeling in which the pore-size distribution is altered to match the capillary injection pressure for different tock types. In addition, for water flooding, contact angles are adjusted to match the measured wettability indices. Gladkikh and Bryant (2004) discuss the use of pore-scale modeling of wetting phase imbibition in porous media. Much of the pioneering work in pore-scale modeling for permeability determination is discussed in papers co-authored by Bryant. What is lacking in prior art is a compact discussion of the interrelation between the different petrophysical parameters that may be determined, and their applicability to hydrocarbon exploration in clastic sediments. The present invention addresses this need.

SUMMARY OF THE INVENTION

One embodiment of the invention is a method of evaluating an earth formation. A distribution of grain sizes is determined from at least one core recovered from a borehole in the earth formation. A pore-scale model of the earth formation is defined using the distribution of grain sizes, and a value of an additional property of the earth formation is determined. The at least one core may be a sidewall core or a bottom-hole core. The at least one core may include more than one directional cores and the at least one additional property may be estimated in more than one direction. The distribution of grain sizes may be obtained by analyzing a thin section of the core, and/or performing a grain size analysis. The distribution of grain sizes may include a distribution of sand grain sizes, a distribution of quartz overgrowth, and/or a distribution of dispersed shale. additional property may be a permeability of the formation. The earth formation may be a laminated formation in which cores are recovered from different laminae. In a laminated formation, the additional property may include a horizontal permeability and a vertical permeability. The definition of the pore scale model may include altering a size of the grains, adding a material to a pore space of the model, replacing a grain of the material, accounting for quartz overgrowth, accounting for pore-filling dispersed shale, accounting for compaction, and/or accounting for calcite overgrowth. The additional property of the formation may be a relation between capillary pressure and a fluid saturation and a permeability may be determined from the relation between the capillary pressure and fluid saturation. The additional property may be a relationship between relative permeability and a fluid saturation, a relative permeability of a non-wetting fluid phase in the earth formation, an end-point mobility of a fluid in the earth formation, and/or a permeability of a first fluid in the earth formation at an irreducible saturation of a second fluid in the earth formation.

Another embodiment of the invention is an apparatus for evaluating an earth formation. The apparatus includes a coring device conveyed in a borehole in the earth formation. The coring device recovers at least one core sample. A processor defines a pore-scale model of the earth formation using a distribution of grain sizes determined from the core sample, and estimates from the pore-scale model a value of an additional property of the earth formation. The coring device may be a sidewall corer, and/or a bottom-hole corer. The at least one core sample further may include more than one core sample oriented in different directions and the processor may estimate the value of the at least one additional property in a more than one direction. The distribution of grain sizes may be determined from analysis of a thin section of the core, and/or grain size analysis. The distribution of grain sizes may include a distribution of sand grain sizes, a distribution of quartz overgrowth, and/or a distribution of dispersed shale. The additional property may include a permeability of the formation. The earth formation may be a laminated formation with cores recovered from different laminae. The processor may determine both horizontal and vertical permeabilities from the multiple cores. The processor may define the pore scale model by altering a size of the grains, adding a material to a pore space of the model, replacing a grain of the material, accounting for quartz overgrowth, accounting for pore-filling dispersed shale, accounting for compaction, and/or accounting for calcite overgrowth. The at least one additional property of the formation may include a relation between capillary pressure and a fluid saturation and permeability may be determined from the relation between capillary pressure and fluid saturation. The additional property may be a relationship between relative permeability and a fluid saturation, a relative permeability of a non-wetting fluid phase in the earth formation, an end-point mobility of a fluid in the earth formation, and/or a permeability of a first fluid in the earth formation at an irreducible saturation of a second fluid in the earth formation. The coring device may be conveyed downhole by a wireline, and/or a drilling tubular.

Another embodiment of the invention is a computer readable medium for use with an apparatus for evaluating an earth formation. The apparatus includes a coring device conveyed in a borehole in the earth formation, the coring device recovering a core sample. The medium includes instructions which enable a processor to define a pore-scale model of the earth formation using a distribution of grain sizes determined from the core sample, and estimate from the pore-scale model a value of an additional property of the earth formation. The computer readable medium may be a ROM, an EPROM, an EAROM, a Flash Memory, and an Optical disk.

BRIEF DESCRIPTION OF THE FIGURES

The present invention is discussed with reference to specific logging instruments that may form part of a string of several logging instruments for conducting wireline logging operations. It is to be understood that the choice of the specific instruments discussed herein is not to be construed as a limitation and that the method of the present invention may also be used with other logging instruments as well. The present invention is best understood with reference to the accompanying figures in which like numerals refer to like elements and in which:

FIG. 4b (prior art) shows the effect of compaction on the arrangement of FIG. 4a;

We begin our discussion of the present invention with an overview of the different types of formation evaluation sensors whose output may be used with the method. This is followed by a discussion of some exemplary prior art methods related to pore-scale modeling of earth formations and their use in predicting macroscopic properties of earth formations that can be measured by formation evaluation sensors. Following this, the method of the present invention is discussed.

Figure 1:
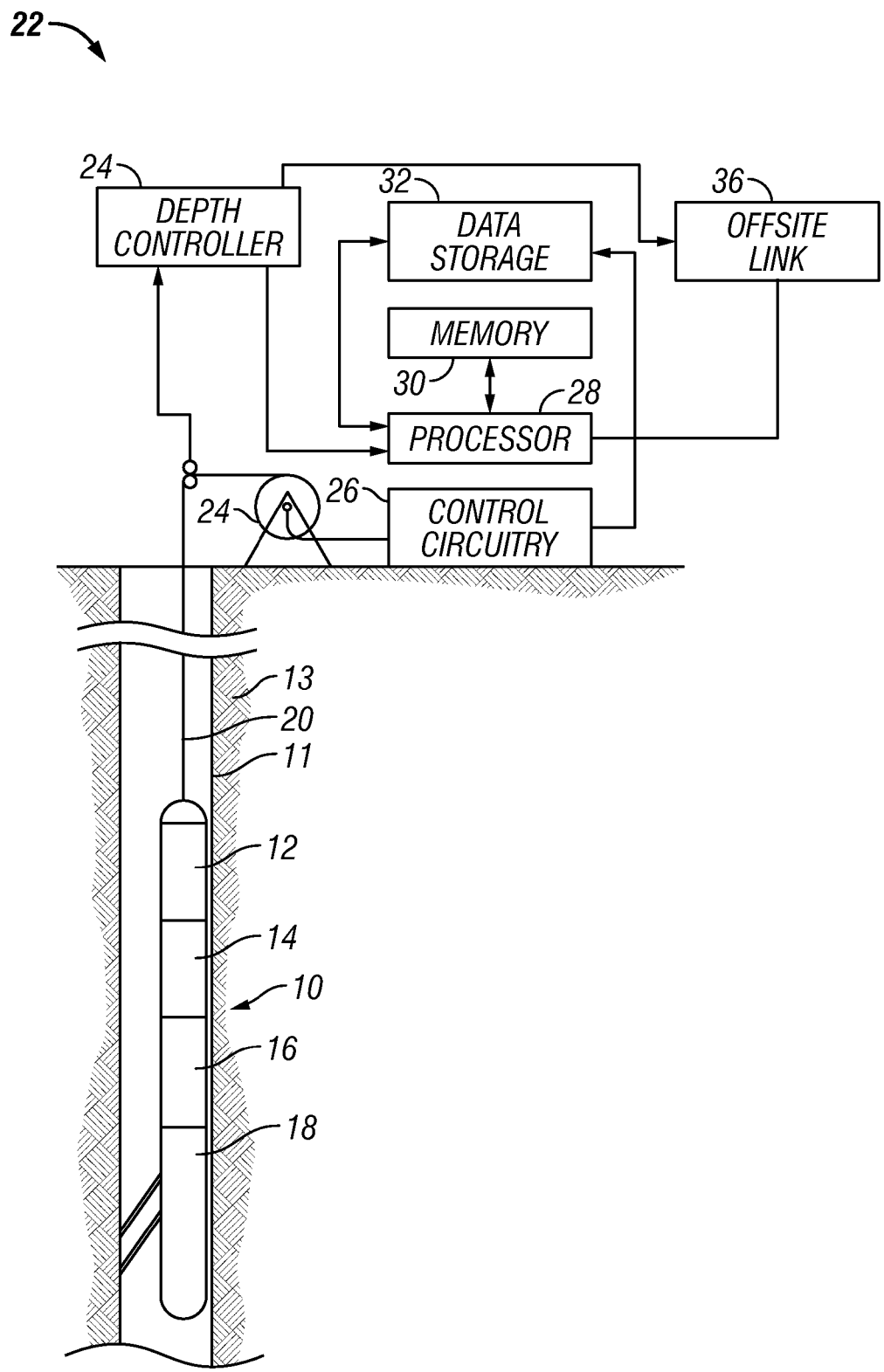
FIG. 1 (prior art) is a schematic illustration of a wireline logging system including a plurality of sensors.

A typical configuration of the logging system is shown in FIG. 1. This is a modification of an arrangement from U.S. Pat. No. 4,953,399 to Fertl et al. having the same assignee as the present invention and the contents of which are incorporated herein by reference. Shown in FIG. 1 is a suite of logging instruments 10, disposed within a borehole 11 penetrating an earth formation 13, illustrated in vertical section, and coupled to equipment at the earth's surface in accordance with the method and apparatus for determining characteristics of clay-bearing formations of the present invention. Logging instrument suite 10 may include a resistivity device 12, a natural gamma ray device 14, and two porosity-determining devices, such as a neutron device 16 and a density device 18. Collectively, these devices and others used in the borehole for logging operations are referred to as formation evaluation sensors. Resistivity device 12 may be one of a number of different types of instruments known to the art for measuring the electrical resistivity of formations surrounding a borehole so long as such device has a relatively deep depth of investigation. For example, a HDIL (High Definition Induction Logging) device such as that described in U.S. Pat. No. 5,452,761 to Beard et al. having the same assignee as the present invention and the contents of which are fully incorporated herein by reference may be used. Natural gamma ray device 14 may be of a type including a scintillation detector including a scintillation crystal cooperatively coupled to a photomultiplier tube such that when the crystal is impinged by gamma rays a succession of electrical pulses is generated, such pulses having a magnitude proportional to the energy of the impinging gamma rays. Neutron device 16 may be one of several types known to the art for using the response characteristics of the formation to neutron radiation to determine formation porosity. Such a device is essentially responsive to the neutron moderating properties of the formation. Density device 18 may be a conventional gamma-gamma density instrument such as that described in U.S. Pat. No. 3,321,625 to Wahl, used to determine the bulk density of the formation. A downhole processor may be provided at a suitable location as part of the instrument suite.

Instrument suite 10 is conveyed within borehole 11 by a cable 20 containing electrical conductors (not illustrated) for communicating electrical signals between instrument suite 10 and the surface electronics, indicated generally at 22, located at the earth's surface. Logging devices 12, 14, 16 and 18 within instrument suite 10 are cooperatively coupled such that electrical signals may be communicated between each device 12, 14, 16 and 18 and surface electronics 22. Cable 20 is attached to a drum 24 at the earth's surface in a manner familiar to the art. Instrument suite 10 is caused to traverse borehole 11 by spooling cable 20 on to or off of drum 24, also in a manner familiar to the art.

Surface electronics 22 may include such electronic circuitry as is necessary to operate devices 12, 14, 16 and 18 within instrument suite 10 and to process the data therefrom. Some of the processing may be done downhole. In particular, the processing needed for making decisions on speeding up (discussed below) for slowing down the logging speed is preferably down downhole. If such processing is done downhole, then telemetry of instructions to speed up or slow down the logging could be carried out substantially in real time. This avoids potential delays that could occur if large quantities of data were to be telemetered uphole for the processing needed to make the decisions to alter the logging speed. It should be noted that with sufficiently fast communication rates, it makes no difference where the decision making is carried out. However, with present data rates available on MWD/LWD, the decision making is preferably done downhole.

Control circuitry 26 contains such power supplies as are required for operation of the chosen embodiments of logging devices within instrument suite 10 and further contains such electronic circuitry as is necessary to process and normalize the signals from such devices 12, 14, 16 and 18 in a conventional manner to yield generally continuous records, or logs, of data pertaining to the formations surrounding borehole 11. These logs may then be electronically stored in data storage 32 prior to further processing. The processor 28 includes the ability, such as that described in U.S. Pat. No. 4,271,356 to Groeschel et al, for separating radiation measurements from natural gamma ray device 14 into individual energy bands centered about energy peaks of selected elemental sources of radiation, preferably the energy peaks of potassium, uranium and thorium. This processing of the natural gamma ray device could also be done by the downhole processor.

Surface electronics 22 may also include such equipment as will facilitate machine implementation of the method of the present invention. Processor 28 may be of various forms but preferably is an appropriate digital computer programmed to process data from logging devices 12, 14, 16 and 18. Memory unit 30 and data storage unit 32 are each of a type to cooperatively interface with processor 28 and/or control circuitry 26. Depth controller 34 determines the longitudinal movement of instrument suite 20 with borehole 11 and communicates a signal representative of such movement to processor 28. The logging speed is altered in accordance with speedup or slowdown signals that may be communicated from the downhole processor, or provided by the surface processor, as discussed below. This is done by altering the rotation speed of the drum 24. Offsite communication may be provided, for example by a satellite link, by the telemetry unit 36.

While running different logging instruments in a single wireline run, the present invention may use a configuration disclosed in U.S. patent application Ser. No. 10/780,167 of Frost et al. filed on Feb. 17, 2004. The teachings of Frost recognize the fact that different logging instruments operate best at different standoffs from the borehole wall.

Figure 2:
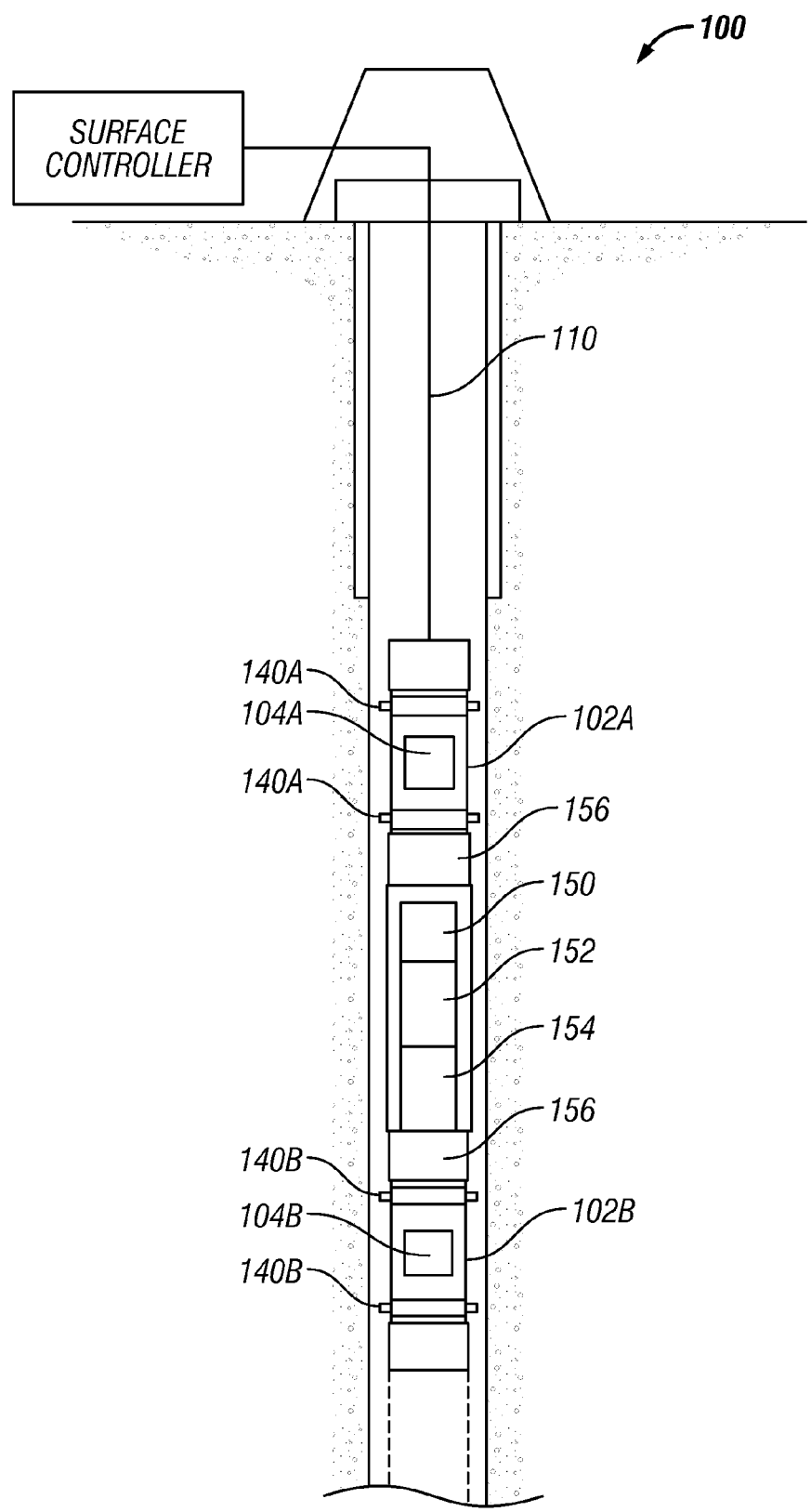
FIG. 2 (prior art) is an elevational view of a system using radially adjustable module adapted for use in logging operations.

Referring next to FIG. 2, there is shown a rig 10 on the surface that is positioned over a subterranean formation of interest. The rig 10 can be a part of a land or offshore a well production/construction facility. A borehole formed below the rig 10 includes a cased portion 42 and an open hole portion 11. In certain instances (e.g., during drilling, completion, work-over, etc.), a logging operation is conducted to collect information relating to the formation and the borehole. Typically, a tool system 100 is conveyed downhole via a wireline 20 to measure one or more parameters of interest relating to the borehole and/or the formation 13. The term "wireline" as used hereinafter includes a cable, a wireline, as well as a slickline. The tool system 100 can include an instrument suite comprising one or more modules 102a,b, each of which has a tool or a plurality of tools 104a,b, adapted to perform one or more downhole tasks. The term "module" should be understood to be a device such as a sonde or sub that is suited to enclose, house, or otherwise support a device that is to be deployed into a borehole. While two proximally positioned modules 102a,b and two associated tools 104a,b, are shown, it should be understood that a greater or fewer number may be used.

In one embodiment, the tool 104a is a formation evaluation sensor adapted to measure one or more parameters of interest relating to the formation or borehole. It should be understood that the term formation evaluation sensor encompasses measurement devices, sensors, and other like devices that, actively or passively, collect data about the various characteristics of the formation, directional sensors for providing information about the tool orientation and direction of movement, formation testing sensors for providing information about the characteristics of the reservoir fluid and for evaluating the reservoir conditions. The formation evaluation sensors may include resistivity sensors for determining the formation resistivity and dielectric constant, acoustic sensors for determining the acoustic porosity of the formation and the bed boundary in formation, nuclear sensors for determining the formation density, neutron porosity and certain rock characteristics, nuclear magnetic resonance sensors for determining the porosity and other petrophysical characteristics of the formation. The direction and position sensors may include a combination of one or more accelerometers and one or more gyroscopes or magnetometers. The accelerometers preferably provide measurements along three axes. The formation testing sensors collect formation fluid samples and determine the properties of the formation fluid, which include physical properties and chemical properties. Pressure measurements of the formation provide information about the reservoir characteristics and the net confining stress.

The tool system 100 can include telemetry equipment 150, a local or downhole controller 152 and a downhole power supply 154. The telemetry equipment 150 provides two-way communication for exchanging data signals between a surface controller 112 and the tool system 100 as well as for transmitting control signals from the surface processor 112 to the tool system 100.

In an exemplary arrangement, and not by way of limitation, a first module 102a includes a tool 104a configured to measure a first parameter of interest and a second module 102b includes a tool 104b that is configured to measure a second parameter of interest that is either the same as or different from the first parameter of interest. In order to execute their assigned tasks, tools 104a and 104b may need to be in different positions. The positions can be with reference to an object such as a borehole, borehole wall, and/or other proximally positioned tooling. Also, the term "position" is meant to encompass a radial position, inclination, and azimuthal orientation. Merely for convenience, the longitudinal axis of the borehole ("borehole axis") will be used as a reference axis to describe the relative radial positioning of the tools 104a,b. Other objects or points can also be used as a reference frame against which movement or position can be described. Moreover, in certain instances, the tasks of the tools 104a,b can change during a borehole-related operation. Generally speaking, tool 104a can be adapted to execute a selected task based on one or more selected factors. These factors can include, but not limited to, depth, time, changes in formation characteristics, and the changes in tasks of other tools.

Modules 102a and 102b may each be provided with positioning devices 140a, 140b1, respectively. The positioning device 140 is configured to maintain a module 102 at a selected radial position relative to a reference position (e.g., borehole axis). The position device 140 also adjusts the radial position of module 102 upon receiving a surface command signal and/or automatically in a closed-loop type manner. This selected radial position is maintained or adjusted independently of the radial position(s) of an adjacent downhole device (e.g., measurement tools, sonde, module, sub, or other like equipment). An articulated member, such a flexible joint 156 which couples the module 102 to the tool system 100 provides a degree of bending or pivoting to accommodate the radial positioning differences between adjacent modules and/or other equipment (for example a processor sonde or other equipment). In other embodiments, one or more of the positioning devices has fixed positioning members.

The positioning device 140 may include a body 142 having a plurality of positioning members 144(a,b,c) circumferentially disposed in a space-apart relation around the body 142. The members 144(a,b,c) are adapted to independently move between an extended position and a retracted position. The extended position can be either a fixed distance or an adjustable distance. Suitable positioning members 144(a,b,c) include ribs, pads, pistons, cams, inflatable bladders or other devices adapted to engage a surface such as a borehole wall or casing interior. In certain embodiments, the positioning members 144(a,b,c) can be configured to temporarily lock or anchor the tool in a fixed position relative to the borehole and/or allow the tool to move along the borehole.

Drive assemblies 146(a,b,c) are used to move the members 144(a,b,c). Exemplary embodiments of drive assemblies 146(a,b,c) include an electro-mechanical system (e.g., an electric motor coupled to a mechanical linkage), a hydraulically-driven system (e.g., a piston-cylinder arrangement fed with pressurized fluid), or other suitable system for moving the members 144(a,b,c) between the extended and retracted positions. The drive assemblies 146(a,b,c) and the members 144(a,b,c) can be configured to provide a fixed or adjustable amount of force against the borehole wall. For instance, in a positioning mode, actuation of the drive assemblies 146(a,b,c) can position the tool in a selected radial alignment or position. The force applied to the borehole wall, however, is not so great as to prevent the tool from being moved along the borehole. In a locking mode, actuation of the drive assembly 146(a,b,c) can produce a sufficiently high frictional force between the members 144(a,b,c) and the borehole wall as to prevent substantial relative movement. In certain embodiments, a biasing member (not shown) can be used to maintain the positioning members 144(a,b,c) in a pre-determined reference position. In one exemplary configuration, the biasing member (not shown) maintains the positioning member 144(a,b,c) in the extended position, which would provide centralized positioning for the module. In this configuration, energizing the drive assembly overcomes the biasing force of the biasing member and moves one or more of the positioning members into a specified radial position, which would provide decentralized positioning for the module. In another exemplary configuration, the biasing member can maintain the positioning members in a retracted state within the housing of the positioning device. It will be seen that such an arrangement will reduce the cross sectional profile of the module and, for example, lower the risk that the module gets stuck in a restriction in the borehole.

The positioning device 140 and drive assembly 146(a,b,c) can be energized by a downhole power supply (e.g., a battery or closed-loop hydraulic fluid supply) or a surface power source that transmits an energy stream (e.g., electricity or pressurized fluid) via a suitable conduit, such as the umbilical 120. Further, while one drive assembly (e.g., drive assembly 146a) is shown paired with one positioning member 144 (e.g., position member 144a), other embodiments can use one drive assembly to move two or more positioning members. The outputs of formation evaluation sensors of the type discussed above, and the outputs of other sensors are used in the present invention in conjunction with pore-scale modeling of earth formations.

Figure 3:
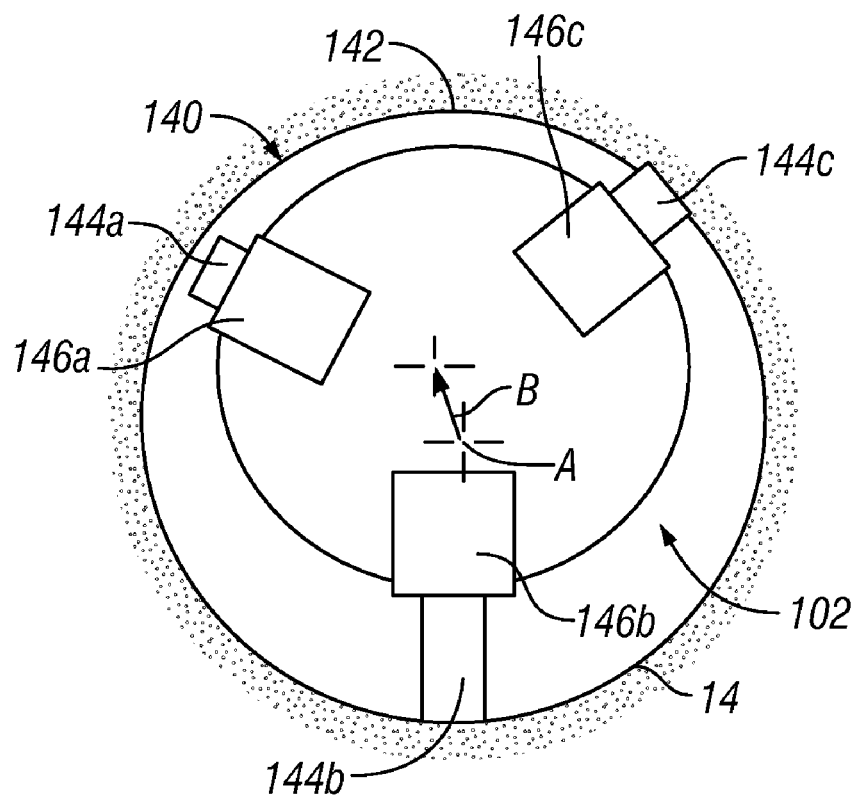
FIG. 3 (prior art) is a cross-sectional view of radially adjustable module positioned in an open hole portion of a borehole.

The method of the present invention is based upon the use of pore-scale modeling together with measurements that may be made by one or more FE sensors including but not limited to the types discussed above with reference to FIGS. 1-3. Before discussing the method of the present invention, we briefly review some of the basic concepts involved in pore-scale modeling.

Sedimentary rocks are traditionally classified using petrographic models. The models are used to distinguish between lithologies differing in mineralogy and matrix materials composed predominately of either terrigenous material or biochemical and inorganic chemical precipitants. The two major lithologies derived from these distinctions are "clastic" versus "carbonate" rocks. The term "carbonate" as used in Ramakrishnan (U.S. Pat. No. 6,088,656) refers to biochemical rocks which are precipitated from water chemistry due to the metabolic processes of organisms. In a broad context, they are commonly referred to as "limestones" however their classification is further refined using other parameters. Carbonate rocks are classified according to their proportion of fine grained carbonate grains (carbonate mud) versus larger grains known as "allochems". Allochems include intraclasts, ooilites, pelloids, and fossil fragments. The most widely used classification is that of Dunham.

In contrast to carbonate classifications, clastic sedimentary rock classifications are based on varying proportions of clasts of different material and grain size composed of minerals and rock fragments. The term "clastic" is derived from a Greek word meaning broken. The accumulation of this terrigenous material is the direct result of the following dynamic subaerial and subaqueous processes: (1) gravity driven mass wasting (downslope slides), (2) winds resulting from atmospheric phenomena such as found in the aeolian environment, (3) gravity driven flowing water (fluvial and alluvial), and (4) tide and wind driven wave energy (nearshore). Subaqueous processes also include (a) gravity driven sedimentation forcing the deposition of suspended sediment onto the floor of water bodies (pelagic and lacustrin sedimentation), (b) thermally forced current flow, and (c) gravity forced turbid flow of water-saturated sediments (turbidity flow). The present invention is directed towards clastic sediments.

Figure 4A:
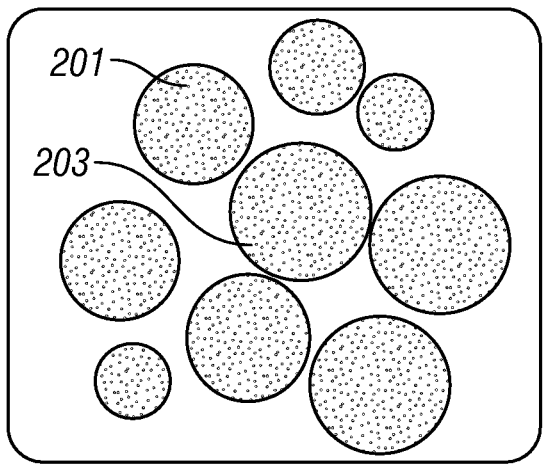
FIG. 4a (prior art) shows a 2-D slice through a random packing of equal spheres.
Figure 4B:
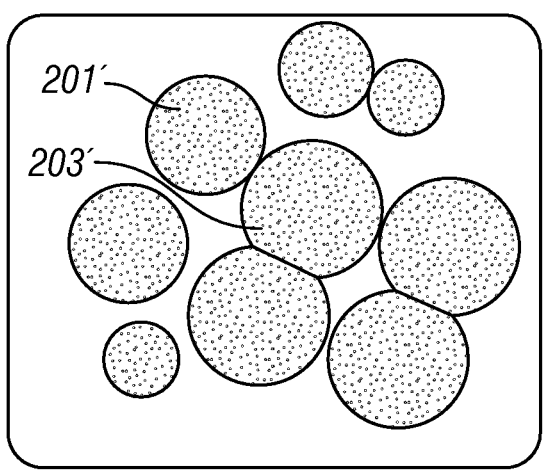
Figure 4C:
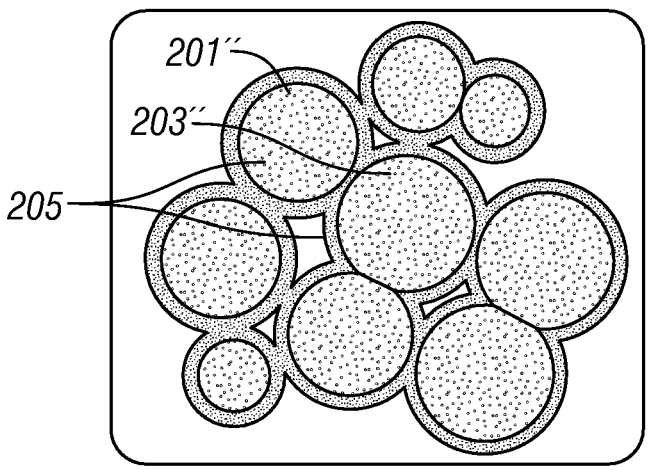
FIG. 4c (prior art) shows quartz overgrowth cementation.

A pore scale model of spheres is the starting point for the characterization of clastic sediments. Shown in FIG. 4a is a 2-D slice through a random packing of equal sized spheres, two of which are denoted as 201, 203. Note that in the 2-D slice, they appear to be of different sizes due to the fact that in the third dimension, they are displaced different distances from the plane of the 2-D slice. Compacting the spheres due to an external stress causes them to interpenetrate as shown by 201', 203'. Note the reduced distance between the spheres. Quartz overgrowth leads to deposition of cement (denoted by 205) and the positions of the two exemplary spheres is now 201", 203". As discussed by Bryant and Raikes, the compaction is equivalent to a rescaling of one of the coordinate axes of Finney:

$$x'_j = x_{j0} + \lambda(x_j - x_{j0}) \quad (1),$$

where $x_{j0}$ is an arbitrary reference value and $\lambda$ quantifies the degree of compaction. A physically reasonable value of $\lambda$ is $0.7 < \lambda < 1.0$, corresponding to a range of 30% to 0% decrease in bulk volume. For simplicity, Bryant and Raikes assume no deformation of the spheres. The cementation by quartz overgrowth is simulated by increasing the radius of the spheres in the packing without altering the location of the sphere centers:

$$R_i' = R_i + \Delta R_i \quad (2),$$

where Ri is the radius of the i-th sphere. In one embodiment of the present invention, it is assumed that all grains grow uniformly, i.e., that $\Delta R$ is constant. This is the assumption made in Bryant and Raikes. In an alternate embodiment of the invention, this assumption is not made. It should be noted that other types of overgrowth, such as calcite overgrowth, may also be part of the model. All that is necessary is to change the elastic properties of the overgrowth material.

Bryant and Raikes next discuss the elastic moduli corresponding to the pore-scale model. Specifically, the Biot-Gassmann theory is used. This theory requires four parameters. They are the porosity $\phi$, the tortuosity $\tau$, the bulk modulus $K_b$ and the grain bulk modulus $G_b$. It should be noted that instead of the bulk moduli, other parameters such as the shear moduli and/or Poisson's ratio may also be used in the formulation.

Figure 5:
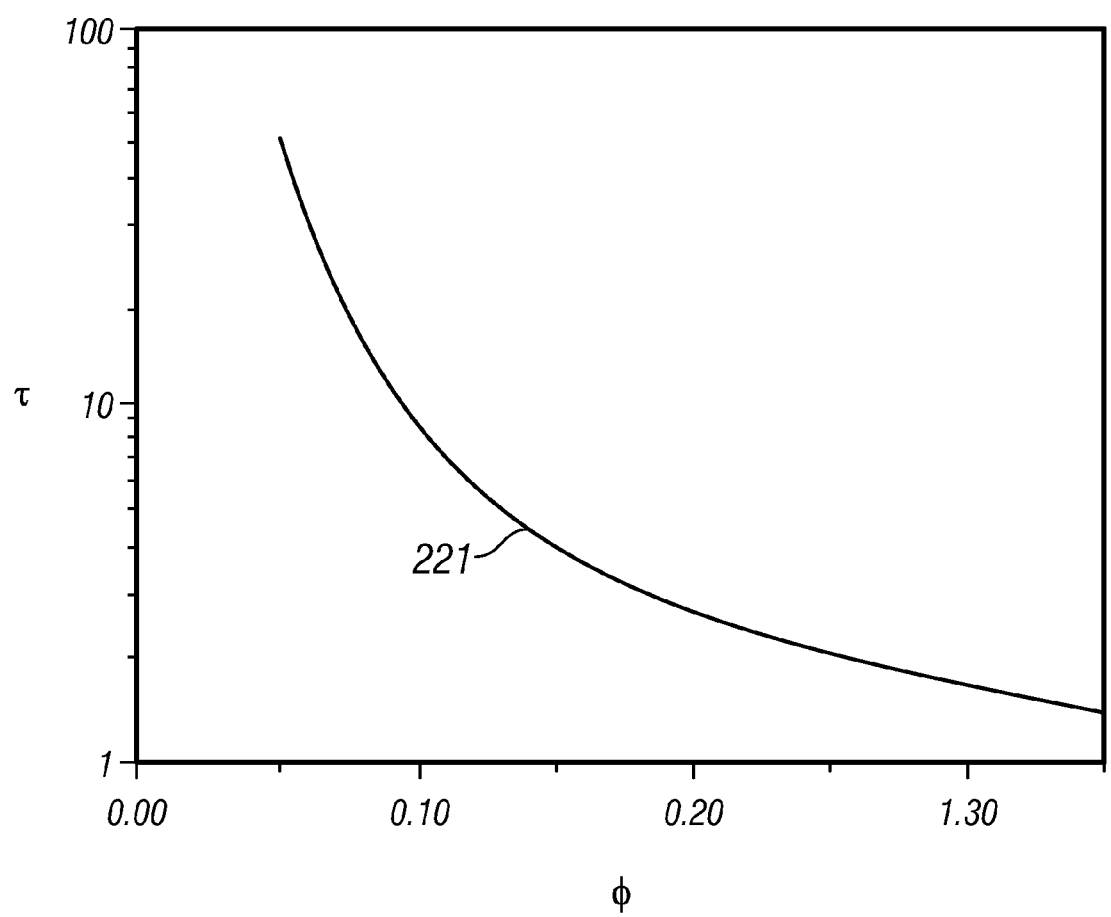
FIG. 5 (prior art) shows tortuosity as a function of porosity for the sandstone model of FIGS. 4a-4c.

Porosity for a particular sphere pack is readily determined from the Delaunay tessellation of the sphere pack. This tessellation is a method of dividing the packing into non overlapping tetrahedral cells. The cells fit together to completely fill the packing volume. The porosity is simply the ratio of the total void volume of the cells to the total volume of the cells. The tortuosity is the product of the porosity and the formation factor. The formation factor can be calculated from a pore-space network extracted from the tessellation without the use of adjustable parameters. FIG. 5a is a plot of the tortuosity 221 as a function of porosity.

To complete the Gassmann calculations, the frame moduli are calculated from Digby's grain-contact theory that requires four microstructural parameters: a, Z, and R. The porosity is determined from the Delaunay cell tessellation described above. Using the known location of each sphere in the compacted/cemented packing, the number of contacts for each sphere and the radius of the area of each contact are readily calculated. The averages of these values over the packing give the values of a and Z. The sphere radius R is fixed by the desired degree of simulated cementation.

Figure 6A:
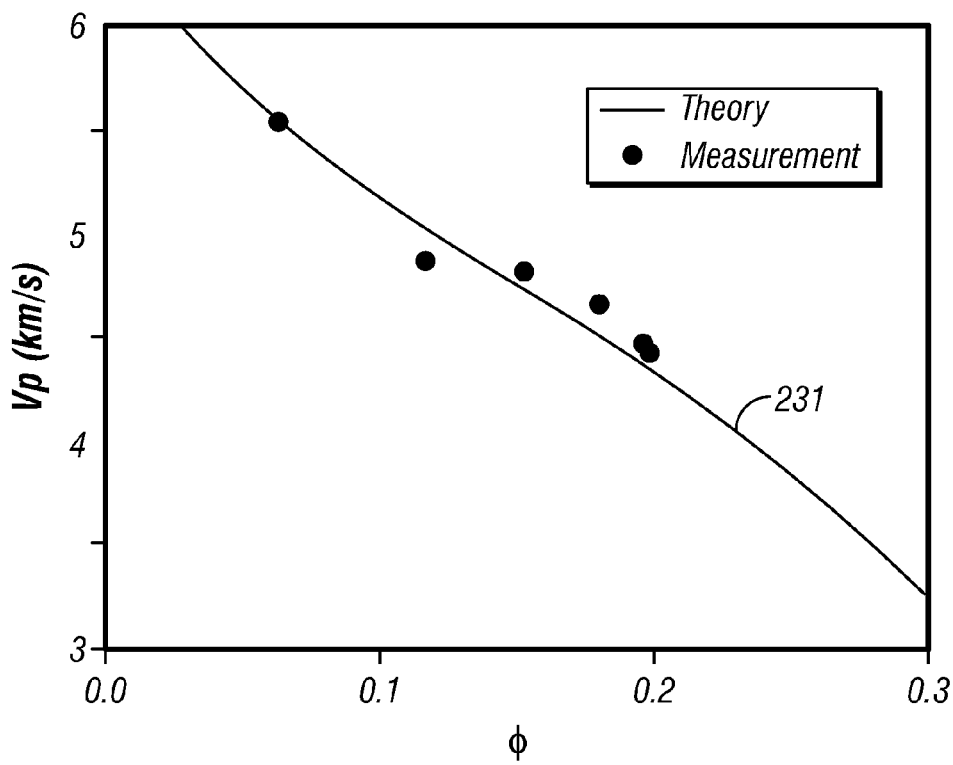
FIGS. 6a and 6b (prior art) show the modeled and actual dependence of compressional and shear wave velocities on porosity.
Figure 6B:
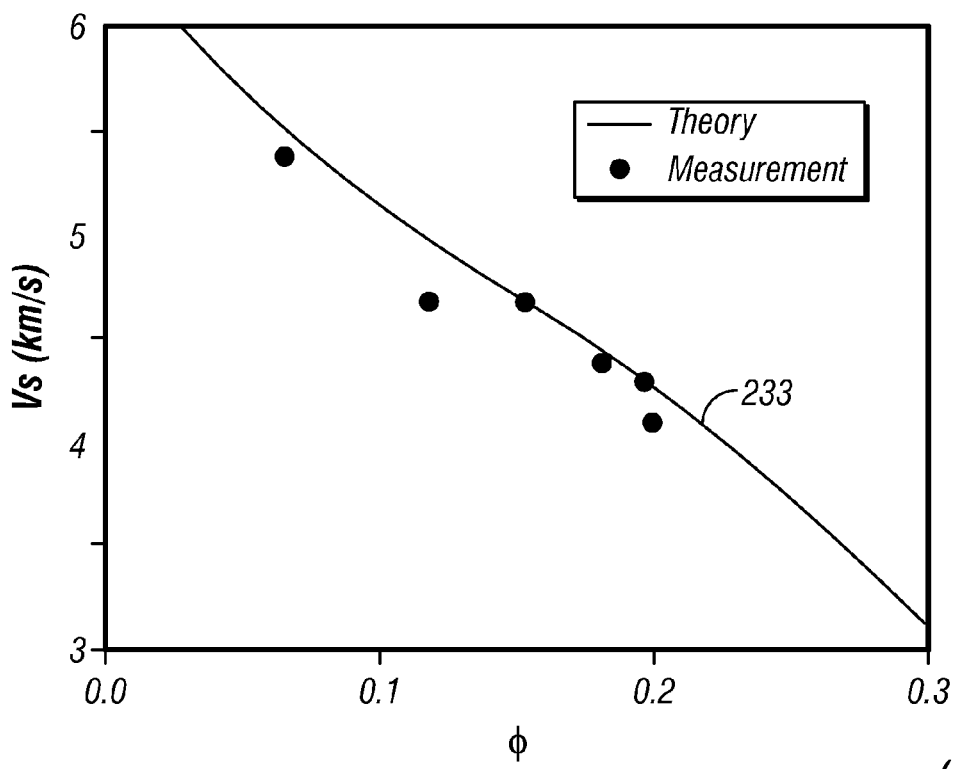

Bryan and Raikes also do calculations of elastic moduli using the Berryman effective medium theory. These are not discussed in detail here and the complete discussion is given in Bryan and Raikes. FIGS. 6a and 6b show plots of the compressional velocity $V_p$ as a function of porosity, and the shear velocity $V_s$ as a function of porosity respectively. The solid curves give the theoretical results for the pore-scale model while the individual points represent actual measurements on sandstones. Agreement is reasonably good. It should be noted that equivalent elastic parameters such as bulk modulus (or its reciprocal, compliance), shear modulus (or its reciprocal, compliance) and/or Poisson's ratio could also be modeled. These equivalent parameters are not easy to measure at normal logging speeds.

In one embodiment of the present invention, the porosity $\phi$ of the pore-geometrical model is adjusted heuristically to mimic known geological processes. This has been discussed in Bryan and Raikes. In addition to the compaction and quartz overgrowth discussed above, the present invention also envisages simulation of shale infilling. The porosity reduction of dispersed shale can be mimicked simply by randomly infilling the pore space. In all of the approaches, the porosity is decreased from the original porosity (~36%)

until it agrees with measured porosity (e.g., wireline and/or MWD or LWD data, sidewall core data).

Given that there are many ways to reduce the porosity of the pore-geometric model one must choose one of the models. In one embodiment of the invention, a log-measured shale indicator, $V_{shale}$ (e.g., from a gamma ray log, SP log, or CBW from NMR measurements) is used. $V_{shale}$ may also be obtained from the difference in porosity derived from a neutron porosity measurement and the porosity derived from a density porosity measurement. In general, $V_{shale}$ can be determined from many log measurements, either singly or in combination. If the $V_{shale}$ indicator exceeds some minimum value then dispersed shale is used to infill the pores until the model $\phi$ and the measured $\phi$ agree. This may be continued until available pore space is infilled. If the apparent $V_{shale}$ is still less than the log indicated $V_{shale}$ then sand grains can be replaced with shale. The approach can be further refined by using a Thomas-Steiber approach to determine the shale distribution. A similar approach can be used to model autogenic shale.

Infilling the inter-granular porosity with shale mimics dispersed shale. It is generally accepted that the shale material contains ineffective porosity which does not contribute to fluid flow but increases the bound water. One can account for the shale porosity in a more complex approach which involves increasing both the pore-filling shale and the grain diameter. For example the volume of dispersed shale can be increased in proportion to the log-measured $V_{shale}$ and in particular it can be increased by randomly adding shale with a given $\phi_{shale}$ until the $\phi_{shale} \cdot V_{shale}$ equals the NMR-derived Clay Bound Water, CBW, and the pore geometric model porosity equals the log measured porosity:

The tessellation method discussed in Bryan and Raikes was originally discussed in Bryant and Blunt for the problem of fluid flow through porous media. Flow in such a porous medium is addressed by dividing the space into tetrahedra defined by the spheres, and defining an equivalent network model of the pore space. The network model now consists of pores or void spaces connected by narrower constrictions or throats. Each cell represents a pore and each cell face is a throat. The aggregation of cell pore volumes is used to calculate the porosity of the network and the fluid saturation when different cells are occupied by different fluids. The flow paths between adjacent cells are modeled by cylinders whose radii and length are hydrodynamically equivalent to the real pore space. The basic relations are:

$$Q = g\Delta P \quad (3),$$

where Q is the volume of fluid entering or leaving the medium in unit time, $\Delta P$ is the pressure drop and g is the hydrodynamic conductivity. For Poiseuille flow in a cylinder of radius r and length l, $$g = \frac{\pi r^4}{8 \mu l}. \quad (4)$$

Figure 7:
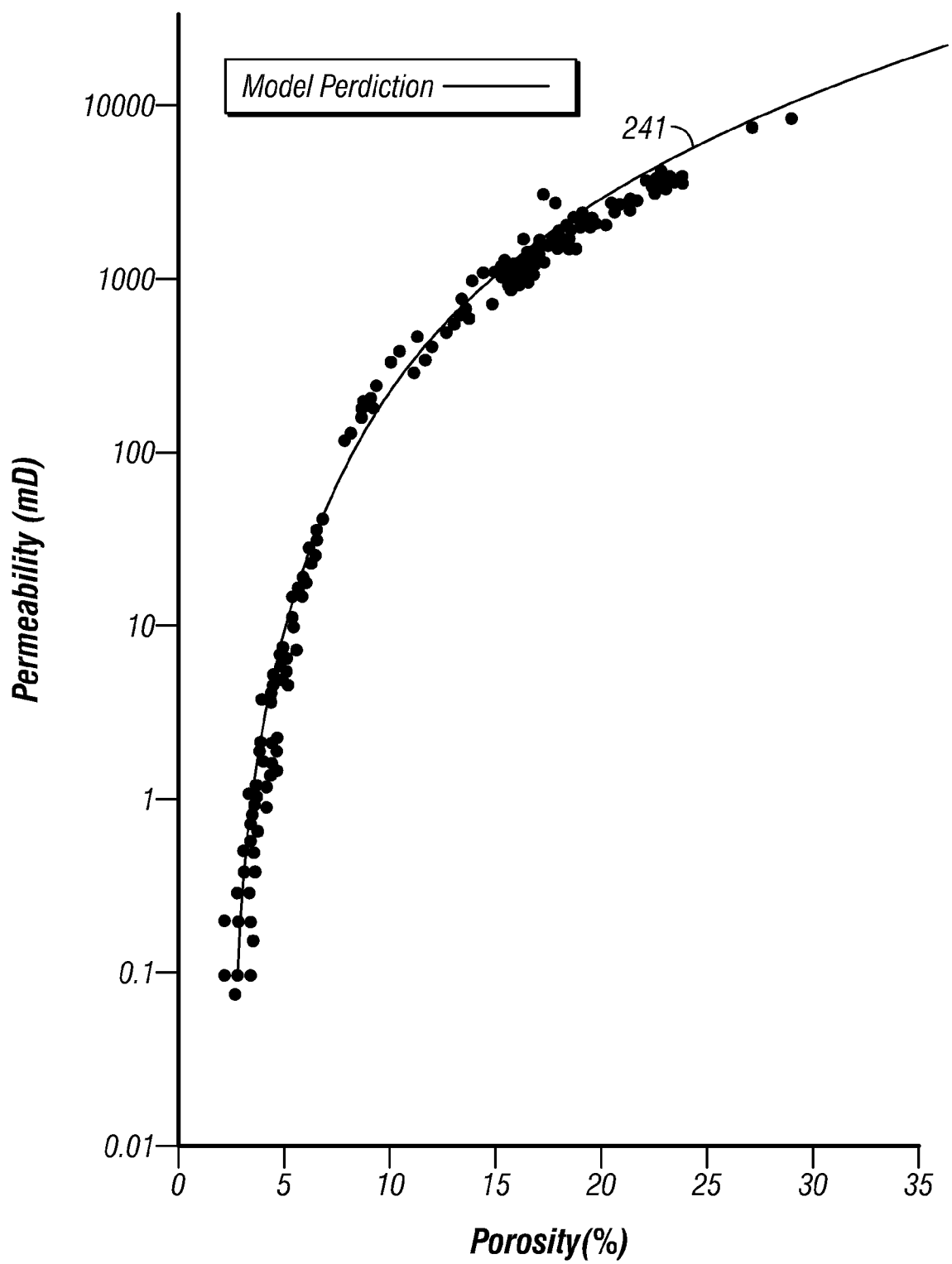
FIG. 7 (prior art) shows a comparison of the modeled and measured permeability as a function of porosity for a sandstone.

Bryant and Blunt show comparisons of their model prediction of permeability as a function of porosity both single phase flow and multiphase flow. FIG. 7 shows such a comparison for measurements made on the Fountainbleau sandstone with the solid line being the model prediction and the individual points are measurements on different samples of the Fountainbleau sandstone. Agreement is good.

For two phase flow, Bryant and Blunt define a wetting phase and a non-wetting phase. They consider the effects of surface tension which results in a contact angle $\theta$ which defines the angle at which the fluid interface approaches a solid surface. Initially, the wetting phase is hydraulically connected throughout the rock along a network of sub-pore-scale roughness. Nonwetting fluid is allowed to access the network through a fraction of the faces or throats chosen at random on the outer boundary of the pack. The model assumes that the nonwetting fluid enters the pack sequentially through throats with successively smaller throat radius. Using this simple model, the mercury permeability injection was simulated. Bryant and Blunt showed a good comparison between predicted and actual values of relative permeability for a wide range of water saturation, different rates of flow for viscous flow and capillary flow. A detailed description of the physics of the model for multiphase flow is found in Blunt et al. (2002).

Another problem in which pore scale modeling has been used is that of prediction of NMR properties of earth formations. Toumelin et al. simulate the NMR response of porous rocks using a continuous, three-dimensional (3D) random-walk algorithm that solves Bloch-Torrey equations. The Bloch-Torrey equations, sometimes called the Bloch equations, describe the macroscopic nuclear magnetization of an assemblage of nuclear spins in a magnetic field. Toumelin solves the Bloch equations along the diffusion pathways of individual fluid molecules within a 3D porous synthetic grain packs designed to be geologically meaningful. The general method discussed by Toumelin provides a rigorous treatment of $T_1$ and $T_2$ relaxations with a minimum of assumptions and for arbitrary pulse sequences. Toumelin also discusses the issue of numerical accuracy of the simulation. The method explicitly accounts for diffusion in porous media, fluid wettabilities, and fluid spatial distributions. Toumelin concluded that currently available 2D NMR methods cannot correctly diagnose substantial diffusion coupling in carbonate rocks.

Figure 8:
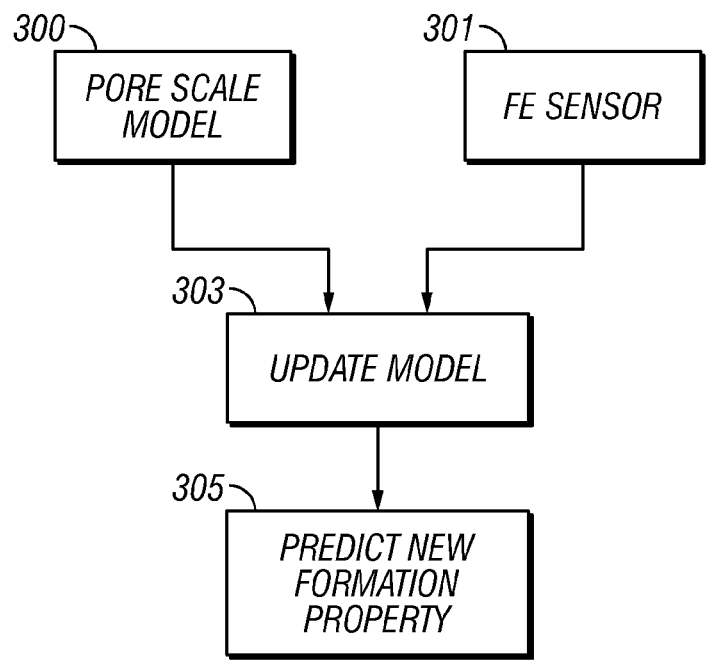
FIG. 8 is flow chart illustrating a method of the present invention using log measurements.

Turning now to FIG. 8, the basic concept underlying one embodiment of the invention is discussed. Measurements are made with a formation evaluation sensor 301 such as an acoustic sensor, a density sensor, a porosity sensor, or a NMR sensor. When acoustic sensors are used, both compressional and shear wave velocities may be measured. When a NMR sensor is used, as noted above, the pulse sequences should be chosen so that estimates of $T_1$, $T_2$ and D are obtained. In certain cases, it may be sufficient to get at least one of $T_1$, $T_2$ and D. The outputs of the FE sensor are matched with the outputs of a pore scale model 300 and based on the comparison, the parameters of the pore scale model are altered 303.

In one embodiment of the invention, the FE sensor is a porosity sensor. The porosity may be determined directly from a neutron porosity device, NMR, or may be inferred from a gamma ray device in combination with knowledge of the lithology of the earth formation. The porosity of the pore-scale model is adjusted to match the observed porosity. Once this has been done, the formation permeability, formation factor and surface to volume (S/V) probability distribution function is calculated. This has been discussed above with reference to FIG. 7 and Bryant and Blunt.

In another embodiment of the invention the FE sensor is a NMR sensor. It is common practice to interpret the NMR data in terms of a pore size distribution. The pore size distribution can then be used in the pore scale model to determine other parameters that are harder to measure.

Figure 9:
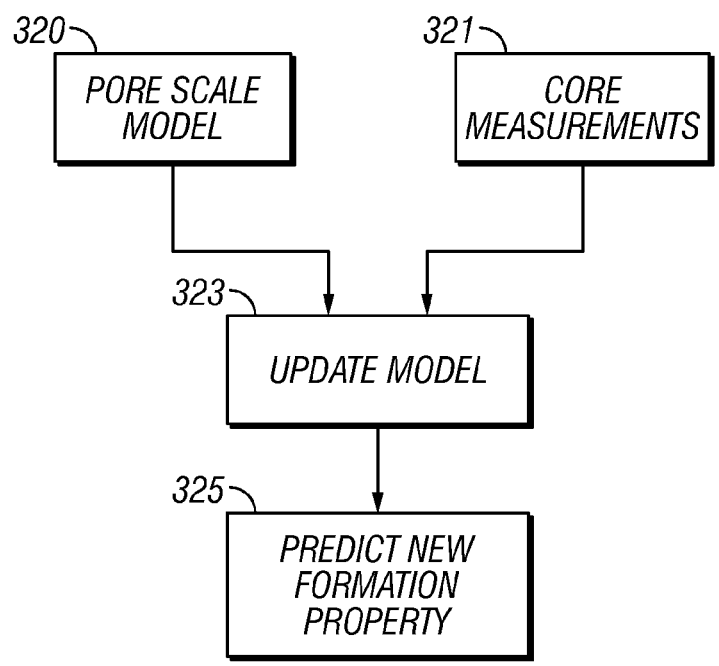
FIG. 9 is a flow chart illustrating a method of the present invention using core measurements.

In another embodiment of the invention shown in FIG. 9, instead of using measurements from a first FE sensor to adjust 323 the pore-scale model 320, core measurements 321 are used. Cores may be obtained from core barrels conveyed at the end of a drillstring or may be sidewall cores obtained using percussion or rotary drilling. Such coring devices are well known in the art. For the purposes of this invention, the coring devices should be such as to maintain the integrity of the core samples so that conventional and/or special analysis of the cores can be made at the surface.

The surface analysis typically involves preparing a thin section of the core sample for examination under a microscope. Based on the examination of the thin sections, porosity and a grain size distribution can be estimated. In addition, the amount of quartz overgrowth can also be determined from a thin section. It is preferable but not essential that the porosity estimate made in surface measurements be corrected for downhole stress conditions. As noted in Domenico (1977), the total change in porosity for a sand pack studied ranged from 0.3817 at 400 psi to 0.3672 at 5000 psi. For consolidated sandstones where quartz overgrowth has cemented the sand grains together, the porosity change is even less due to the high elastic modulus of quartz. The thin section observations may include the amount of dispersed shale in the core, the determined values being part of the pore-space model and may be used for permeability calculations.

Using the parameters determined from the thin sections, it is possible to predict 325 in situ properties such as permeability using the method of Bryant et al. (1973) without making flow measurements on either the core sample, or flow measurements in the well. One problem of interest is in laminated reservoirs where there is vertical heterogeneity. By obtaining core samples from the different layers and estimating permeability in the different layers, estimates may be made of the bulk permeability in horizontal and vertical directions. As is well known, the horizontal permeability in a laminated reservoir is a weighted average of the permeabilities in the individual layers. The permeability in a direction perpendicular to bedding is obtained by a weighted average of the reciprocals of the permeability. In one embodiment of the invention, a particle size analysis of the core is used to adjust the pore geometric model. The grain size analysis may be done using a laser particle size analysis (LPSA) or a sieve analysis.

Figure 10:
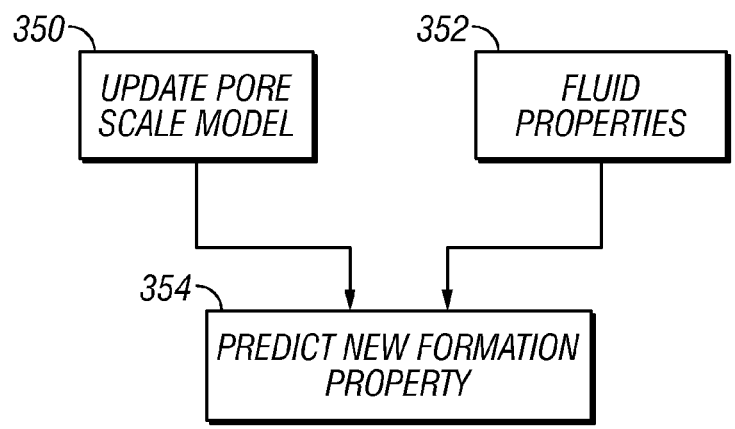
FIG. 10 is a flow chart illustrating a method of the present invention in which a pore scale model is used to derive additional formation properties using values of properties of a fluid in the pore space.
Figure 11:
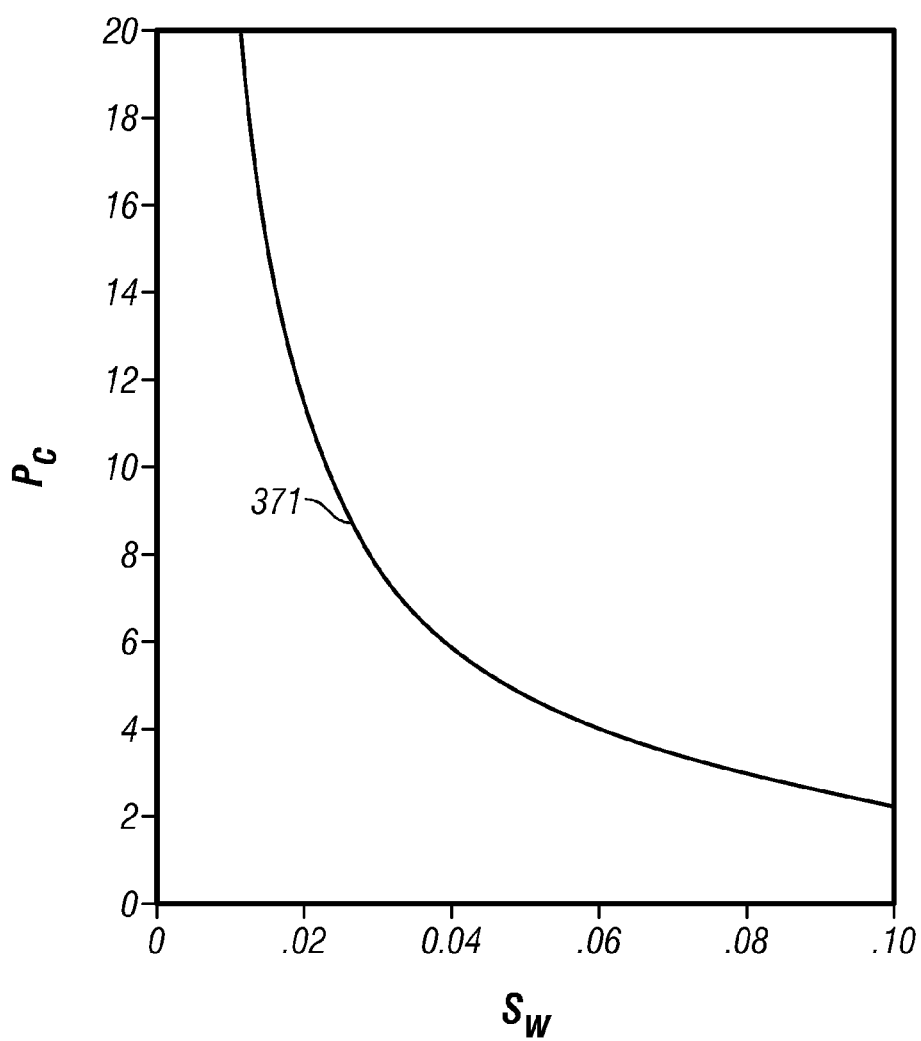
FIG. 11 is an exemplary plot of capillary pressure as a function of fluid saturation derived from a pore scale model and assumed values of interfacial surface tension.

Another embodiment of the invention (FIG. 10) starts with an updated pore scale model of rock properties 350 and uses obtained fluid properties 352 to determine properties of a reservoir 354. The fluid properties may be obtained, for example, from NMR measurements (in situ or on recovered formation fluids), and/or from measurements made on recovered formation fluids. Formation fluids can be recovered, for example, using the method and apparatus described in U.S. Pat. No. 5,303,775 of Michaels et al., U.S. Pat. No. 6,557,632 to Cernosek, or U.S. Pat. No. 6,157,893 to Berger et al. The first three are example of wireline devices while the last one is an example of a MWD device. Specific examples of determination of reservoir properties are discussed next.

In one embodiment of the invention, a relation between capillary pressure and water saturation may be determined. As noted in Hirasaki (3-1), the capillary pressure $P_c$ across an interface is given by $$P_c = \frac{2\sigma}{r} \quad (5)$$

where $\sigma$ is the interfacial surface tension. The pore scale model discussed above gives a pore size distribution model from which a fluid saturation such as water saturation $S_w$ may be determined. Eqn. (5) also gives a direct relation between the pore size and the capillary pressure. Thus, it is possible to derive a relation between capillary pressure and fluid saturation from the pore scale model and knowledge of the interfacial surface tension. Using an assumed value of $\sigma$ (or value of $\sigma$ determined by other means) and the previously determined pore size distribution, the capillary pressure distribution can be obtained, and thus the water saturation that gives the capillary pressure is obtained.

From knowledge of the capillary pressure curve (obtained above using the cumulative distribution of pore radii), the water saturation as a function of elevation above the free water level can be calculated. As noted in Hirasaki (3-3), this requires satisfying the condition:

$$P_c(S_w) = (\rho_w - \rho_o)gh \quad (6),$$

where the $\rho$'s are densities (subscript w refers to water and subscript o refers to oil or hydrocarbon), g is the acceleration due to gravity and h is the height of the water column having a saturation $S_w$.

Figure 12:
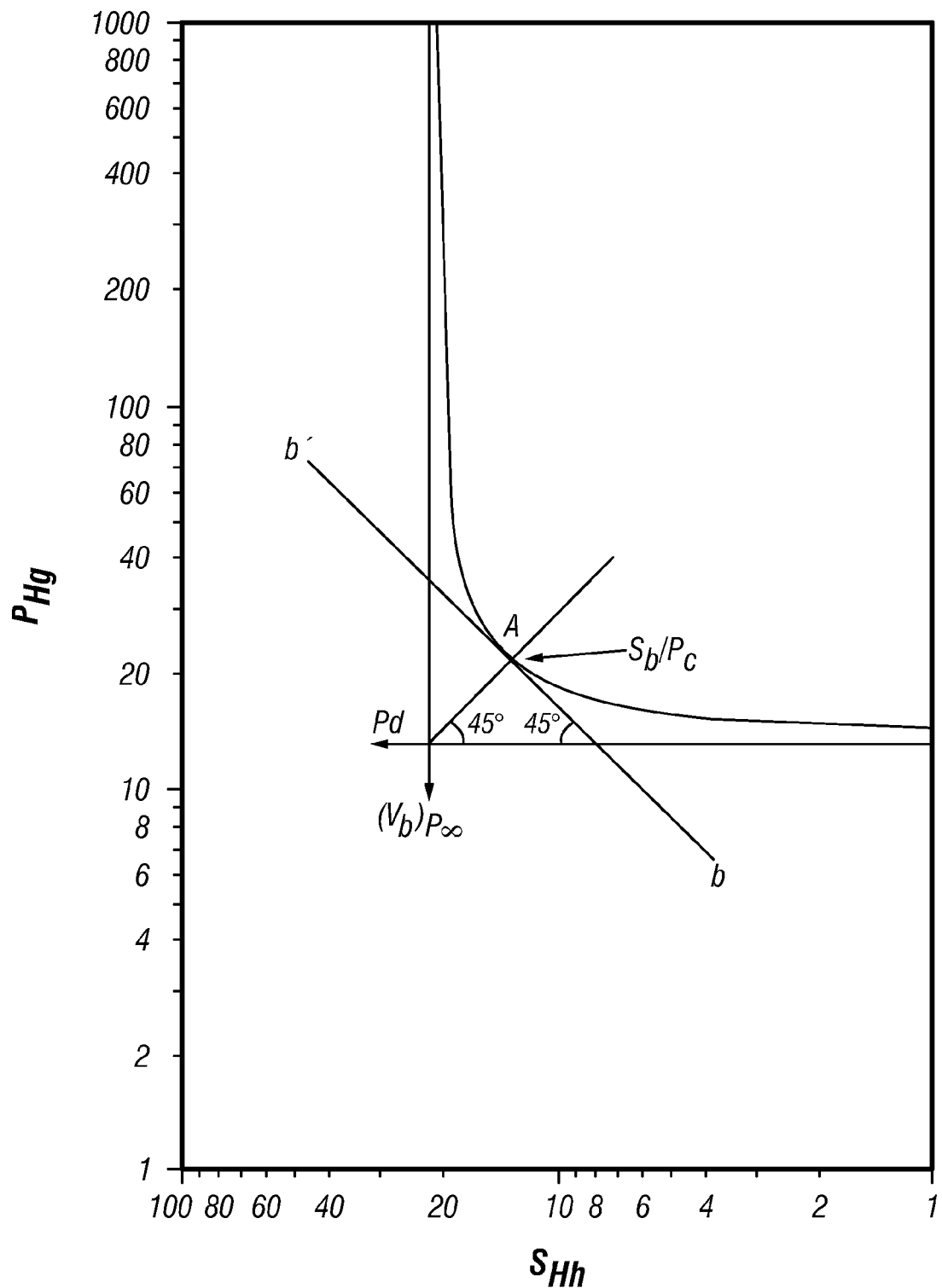
FIG. 12 is a plot useful in determining brine permeability from a capillary pressure-saturation curve.

In another embodiment of the invention, brine permeability may be estimated for a particular pore scale model. One method uses a methodology developed by Swanson. The $P_c$-S relation is developed for mercury using the method outlined above. As disclosed by Swanson, this relation is plotted on a log-log scale. On the log-log plot, the particular ratio of $S_b/P_c$ at which the plot is asymptotic to a 45° line is determined (see FIG. 12). The brine permeability is then given by a relationship of the form:

$$K_w = C\left(\frac{S_b}{P_c}\right)^B, \quad (7)$$

where B and C are calibration constants and $K_w$ is the brine permeability. It should be noted that the particular form of eqn. (7) is not to be construed as a limitation to the method: what is important is that the brine permeability can be determined from a mercury saturation curve that is derivable from the pore scale geometric model.

The present invention also envisages determination of relative permeabilities of a mixture of fluids. An exemplary method is given by Purcell using the Pc-S curves as:

$$k_{rw} = \frac{\int_0^{S_w} dS_w/(P_c)^2}{\int_0^1 dS_w/(P_c)^2} \quad (8)$$

where $k_{rw}$ and $S_w$ are the relative permeability and saturation of the wetting phase. Similarly, the relative permeability of the nonwetting phase is given by:

$$k_{ro} = \frac{\int_{S_w}^1 dS_w/(P_c)^2}{\int_0^1 dS_w/(P_c)^2}. \quad (9)$$

It should be noted that the method given by Purcell is only for exemplary purposes, and other relations such as those from Burdine or Corey may be used. The Burdine model introduces a tortuousity factor $\lambda_{rw}$ of the wetting phase:

$$k_{rw} = (\lambda_{rw})^2 \frac{\int_0^{S_w} dS_w/(P_c)^2}{\int_0^1 dS_w/(P_c)^2}, \quad (10)$$

where $$\lambda_{rw} = \frac{\tau_w(1.0)}{\tau_w(Sw)} = \frac{S_w - S_m}{1 - S_m} \quad (11)$$

where Sm is the minimum wetting phase saturation from the capillary pressure curve, $\tau_w(1.0)$ and $\tau_w(S_w)$ are the tortuousities of the wetting phase when the wetting phase saturation is equal to 100% and Sw respectively. Other models such as the Corey model and/or the Corey-Brooks model may also be used.

Figure 13:
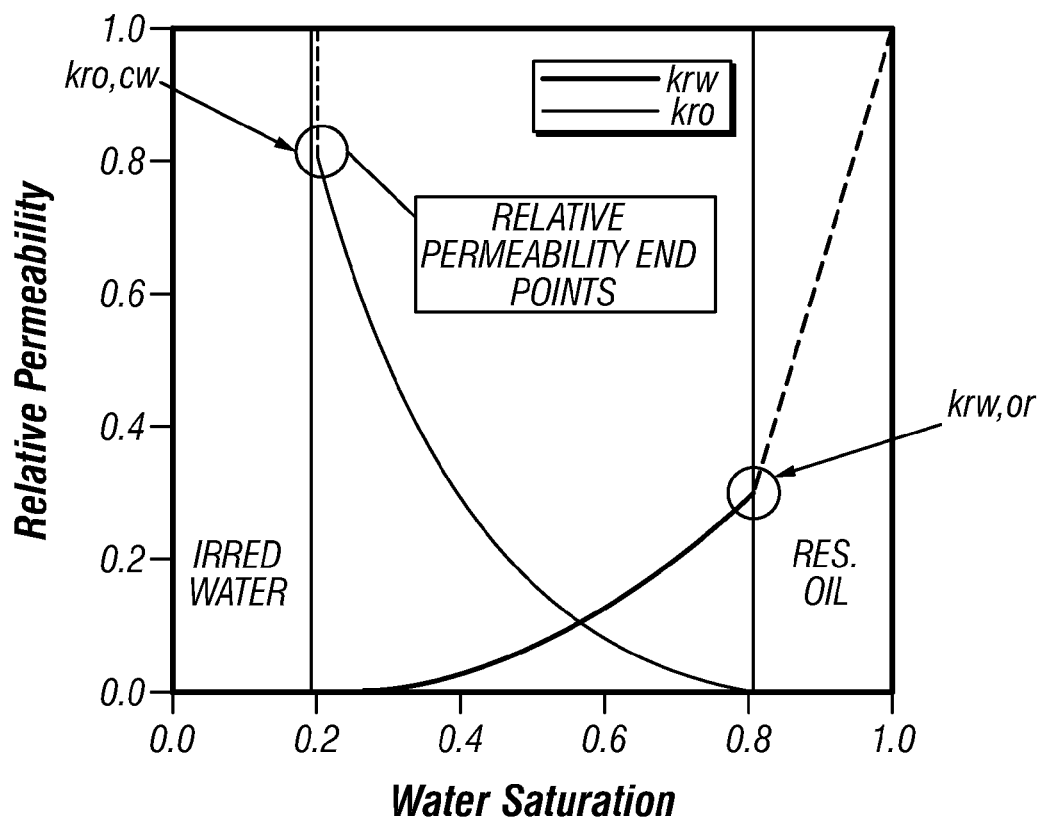
FIG. 13 shows plots of relative permeabilities for a two phase mixture of fluids in the pore space of a rock formation.

End point mobility may also be determined using an assumed value of viscosity (or a measured value such as from NMR measurements). As seen in FIG. 13, there are two end-point relative permeabilities. The first is the relative permeability of hydrocarbons (i.e., oil or gas) at irreducible water saturation $k_{ro,swirr}$ and is of interest when drilling in water-wet zones using an oil-based mud. The other is the relative permeability of water at residual oil saturation $k_{rw,or}$. The latter quantity is of interest in secondary recovery operations and when drilling in hydrocarbon zones using a water-based mud. Corresponding to these endpoints, we have mobilities defined by:

$$M_1 = \frac{k_{rw,or}}{\mu_w} \quad (11)$$

$$M_2 = \frac{k_{ro,swirr}}{\mu_o},$$

and the end-point mobility ratio $M=M_1/M_2$. The quantity $k_{rw,or}$ is of particular interest in water flooding projects where the oil saturation is at residual saturation.

In one embodiment of the invention, directional measurements are made. These directional measurements can be made using directional FE sensors. Alternatively, directional core analysis is done, either from oriented sidewall cores or by azimuthal sampling of bottom-hole cores. This makes it possible to develop pore-scale geometric models that are azimuthally dependent, and thus predict azimuthally dependent properties of the reservoir. Measurements made by orientation sensors discussed above are used in this determination of azimuthal properties.

The invention has been described above with reference to a device that is conveyed on a wireline into the borehole. The method of the invention may also be used with a multicomponent induction logging device conveyed into a borehole on a tubular, such as a drillstring. The processing of the data may be done downhole using a downhole processor at a suitable location. It is also possible to store at least a part of the data downhole in a suitable memory device, in a compressed form if necessary. Upon subsequent retrieval of the memory device during tripping of the drillstring, the data may then be retrieved from the memory device and processed uphole.

Implicit in the control and processing of the data is the use of a computer program on a suitable machine readable medium that enables the processor to perform the control and processing. The machine readable medium may include ROMs, EPROMs, EEPROMs, Flash Memories and Optical disks.

While the foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of evaluating an earth formation, the method comprising:
   (a) defining a pore-scale model of the earth formation having a distribution of grain sizes;
   (b) using data from at least one core for updating the pore-scale model; and
   (c) estimating from the pore-scale model after the updating value of at least one property of the earth formation.

2. The method of claim 1 wherein the at least one core is selected from the group consisting of (i) a sidewall core, and (ii) a bottom-hole core.

3. The method of claim 2 wherein the at least one core comprises a plurality of directional cores and wherein estimating a value of the at least one property of the earth formation further comprises estimating a plurality of values of the at least one property in a plurality of directions.

4. The method of claim 1 wherein using data from at least one core further comprises at least one of (i) analyzing a thin section of the core, and (ii) performing a grain size analysis.

5. The method of claim 1 wherein the distribution of grain sizes further comprises at least one of (i) a distribution of sand grain sizes, (ii) a distribution of quartz overgrowth, and (iii) a distribution of dispersed shale.

6. The method of claim 1 wherein the at least one property comprises a permeability of the formation.

7. The method of claim 1 wherein the earth formation comprises a laminated formation and wherein the at least one core further comprises a plurality of cores in different laminae.

8. The method of claim 6 wherein the laminated formation comprises two constituent materials, and wherein the at least one property comprises a horizontal permeability and a vertical permeability.

9. The method of claim 1 wherein defining the pore-scale model further comprises at least one of (i) altering a size of the grains, (ii) adding a material other than the material to a pore space of the model, (iii) replacing a grain of the material with a different material, (iv) accounting for quartz overgrowth, (v) accounting for pore-filling dispersed shale, (vi) accounting for compaction, and (vii) accounting for calcite overgrowth.

10. The method of claim 1 wherein the at least one property of the formation comprises a relation between capillary pressure and a fluid saturation.

11. The method of claim 10 wherein the at least one property further comprises a permeability determined from the relation between capillary pressure and fluid saturation.

12. The method of claim 1 wherein the at least one property is selected from the group consisting of (i) a relationship between relative permeability and a fluid saturation, (ii) a relative permeability of a non-wetting fluid phase in the earth formation, (iii) an end-point mobility of a fluid in the earth formation, (iv) a permeability of a first fluid in the earth formation at an irreducible saturation of a second fluid in the earth formation.

13. An apparatus for evaluating an earth formation, the apparatus comprising:
(a) a coring device conveyed in a borehole in the earth formation, the coring device recovering at least one core; and
(b) a processor which:
(A) defines a pore-scale model of the earth formation having a distribution of grain sizes
(B) uses data from the at least one core for updating the pore-scale model; and
estimates from the pore-scale model after the updating a value of at least one property of the earth formation.

14. The apparatus of claim 13 wherein the coring device is selected from the group consisting of (i) a sidewall corer, and (ii) a bottom-hole corer.

15. The apparatus of claim 13 wherein the at least one core further comprises a plurality of cores oriented in a plurality of directions and wherein the processor estimates the value of the at least one property in the plurality of directions.

16. The apparatus of claim 13 wherein the processor updates the distribution of grain sizes using at least one of (i) an analysis of a thin section of the core, and (ii) a grain size analysis.

17. The apparatus of claim 13 wherein the distribution of grain sizes further comprises at least one of (i) a distribution of sand grain sizes, (ii) a distribution of quartz overgrowth, and (iii) a distribution of dispersed shale.

18. The apparatus of claim 13 wherein the at least one property comprises a permeability of the formation.

19. The apparatus of claim 13 wherein the earth formation comprises a laminated formation and wherein the at least one core further comprises a plurality of cores in different laminae.

20. The apparatus of claim 19 wherein the laminated formation comprises two constituent materials, and wherein the at least one property comprises a horizontal permeability and a vertical permeability.

21. The apparatus of claim 13 wherein the processor updates the pore scale model by at least one of (i) altering a size of the grains, (ii) adding a material other than the material to a pore space of the model, (iii) replacing a grain of the material with a different material, (iv) accounting for quartz overgrowth, (v) accounting for pore-filling dispersed shale, (vi) accounting for compaction, and (vii) accounting for calcite overgrowth.

22. The apparatus of claim 13 wherein the at least one property of the formation comprises a relation between capillary pressure and a fluid saturation.

23. The apparatus of claim 22 wherein the at least one property further comprises a permeability determined from the relation between capillary pressure and fluid saturation.

24. The apparatus of claim 22 wherein the at least one property is selected from the group consisting of (i) a relationship between relative permeability and a fluid saturation, (ii) a relative permeability of a non-wetting fluid phase in the earth formation, (iii) an end-point mobility of a fluid in the earth formation, (iv) a permeability of a first fluid in the earth formation at an irreducible saturation of a second fluid in the earth formation.

25. The apparatus of claim 13 wherein the coring device is conveyed downhole by one of (i) a wireline, and (ii) a drilling tubular.

26. A computer readable medium for use with an apparatus for evaluating an earth formation, the apparatus comprising:
(a) a coring device conveyed in a borehole in the earth formation, the coring device recovering a core;
the medium comprising instructions which enable a processor to:
(b) define a pore-scale model of the earth formation using a distribution of grain,
(c) use data from the core for updating the pore-scale model; and
(d) estimate from the pore-scale model a value of at least one property of the earth formation.

27. The computer readable medium of claim 26 further comprising at least one of (i) a ROM, (ii) an EPROM, (iii) an EAROM, (iv) a Flash Memory, and (v) an Optical disk.

* * * * *